United States Patent
Nakata et al.

(10) Patent No.: US 7,094,414 B2
(45) Date of Patent: Aug. 22, 2006

(54) FAMOTIDINE INJECTIONS

(75) Inventors: Katsunori Nakata, Yaizu (JP); Hiroshi Yatabe, Yaizu (JP); Tsukasa Nishikawahara, Yaizu (JP)

(73) Assignee: Astellas Pharma Inc., Tokyo (JP)

( * ) Notice: Subject to any disclaimer, the term of this patent is extended or adjusted under 35 U.S.C. 154(b) by 186 days.

(21) Appl. No.: 10/451,402

(22) PCT Filed: Dec. 20, 2001

(86) PCT No.: PCT/JP01/11171

§ 371 (c)(1),
(2), (4) Date: Jun. 23, 2003

(87) PCT Pub. No.: WO02/051411

PCT Pub. Date: Jul. 4, 2002

(65) Prior Publication Data

US 2004/0067993 A1   Apr. 8, 2004

(30) Foreign Application Priority Data

Dec. 22, 2000  (JP) ............. 2000-389887

(51) Int. Cl.
    *A61K 9/00*   (2006.01)
    *A61N 43/78*  (2006.01)
(52) U.S. Cl. .............. 424/400; 514/370; 514/471
(58) Field of Classification Search ............. 424/400, 424/401, 470; 514/370, 471
    See application file for complete search history.

(56) References Cited

U.S. PATENT DOCUMENTS 4,684,630 A * 8/1987 Repta et al. .......... 514/49
5,536,735 A * 7/1996 Takechi et al. ........ 514/338
5,650,421 A   7/1997 Titus et al.
6,147,122 A * 11/2000 Mirejovsky et al. .... 514/731

FOREIGN PATENT DOCUMENTS

| CA | 1184495 A    | 3/1985 |
| EP | 1002531 A1   | 5/2000 |
| JP | 4612756 B    | 4/1971 |
| JP | 11-193233 A  | 7/1999 |

OTHER PUBLICATIONS

Kakemi, K. Absorption of Drugs from the Skeletal Muscle of the Rats. *Faculty of Pharmaceutical Sciences, Kyoto University*, Mar. 10, 1971.
Kakemi, K. Absorption of Drugs form the Skeletal Muscle of the Rats. Effect of Water-soluble Adjuvants and Vehicles on the Intramusclar Absorption. *Faculty of Pharmaceutical Sciences, Kyoto University*, Jun. 15, 1971.
Kobayashi, H. Effect of Some Ionic and Nomionic Sufactants on the Intramusclar Absorption of Isonicotinamide. *Faculty of Pharmaceutical Sciences, Kyoto University*, May 25, 1974.
Kobayashi, H. Effect of Various Alcohols on the Intramusclar Absorption of Isonicofinamide in the Rat. *Faculty of Pharmaceutical Sciences, Kyoto University*, Feb. 12, 1977.
Journal of Pharmaceutical Science and Technology, Japan, (1989), 49 (1), pp. 90 to 101.

* cited by examiner

*Primary Examiner*—Michael G. Hartley
(74) *Attorney, Agent, or Firm*—Sughrue Mion, PLLC

(57) ABSTRACT

The present invention exhibits a remarkable effect of making it possible to provide a famotidine injection solution containing famotidine at a high concentration, being stable for a long period of time at room temperature, and having a low viscosity without impairing the absorption of famotidine, which can be hardly provided so far.

11 Claims, 3 Drawing Sheets

FAMOTIDINE INJECTIONS

TECHNICAL FIELD

The present invention relates to an injection solution containing famotidine or its salt. More specifically, the invention relates to a famotidine injection solution containing famotidine or its salt in an amount of about 1 mg/ml to about 40 mg/ml in terms of the base, further containing a water-soluble acid amide in an amount of about 1 mg to about 30 mg per 1 mg of famotidine, and an acidic substance and having a pH of about 5.5 to about 7.5 and a kinematic viscosity at room temperature of about 0.9 centistokes or more to about 3 centistokes or less.

BACKGROUND ART

Famotidine is a pharmaceutical agent excellent in inhibitory action of gastric acid secretion based on a histamine H2-receptor antagonistic action and generally used in the form of an oral or injection preparation as an agent for treating gastric ulcer, duodenal ulcer, and other digestive diseases (cf. Merck Index thirteen edition, page 696 and so on). With regard to famotidine injection preparations, two kinds of preparations, i.e., a solution preparation and a freeze-dried preparation are present. The solution preparation is commercially available in United States and Europe for intravenous administration, and the freeze-dried preparation is commercially available in Japan as an administration system mainly for intravenous administration and is also used for intramuscular administration. However, an injection solution capable of being preserved at room temperature and capable of being administered intramuscularly is not commercially available.

Famotidine is a basic compound having a pKa value of about 7.1, and it is soluble in water but exhibits a low stability at an acidic side while the solubility extremely decreases at a neutral range where the stability is high.

Hitherto, in the vicinity of a neutral pH range where famotidine exhibits a good stability, various attempts to develop an injection preparation wherein famotidine is solubilized and stable have been made. However, in the case of intramuscular administration, since the administration is physically difficult when a dose is a large amount, the liquid amount to be administered is limited. Usually, the amount is about 4 ml at most. A famotidine injection solution for intramuscular administration requires that solubilization and stabilization of famotidine are achieved even in a small liquid amount (e.g., 3 ml) and further the absorbability does not decreases. Such famotidine injection solution capable of being administered intramuscularly is not yet known.

With regard to famotidine injection preparations, the following technologies are known.

JP-B-63-65047 (or CA1184495) describes the following: a low water-solubility (solubility of 0.1 w/v % or lower) of famotidine makes development of its injection preparation difficult; selection of a substance capable of solubilizing famotidine in a high concentration is necessary for developing the injection preparation; although selection of an acid is considered, selection of an acid capable of not only solubilizing famotidine but also stabilizing is necessary since it is unstable in an acidic region; a stable injection preparation dissolving famotidine in a high concentration (10 mg/ml) can be first provided when a specific acid, L-aspartic acid, is mixed; and so forth. The famotidine injection preparation in clinical use at present is a freeze-dried preparation produced based on the patented invention and it main administration route is intravenous administration. However, in general, a freeze-dried preparation should be prepared before use employing a physiologically allowable dissolution liquid such as physiological saline, and thus it can be said that the preparation is a preparation accompanied by vexatious complication.

In this connection, the pH of the solution obtained by dissolving the freeze-dried preparation in water for injection is about 5.2.

In addition, U.S. Pat. No. 5,650,421 discloses an injection preparation wherein the concentration of famotidine or it salt is from 0.1 mg/ml to 0.8 mg/ml, the pH is adjusted to from 5.7 to 6.4 by adding an acid such as L-aspartic acid, and the preparation is mixed with physiological saline in advance. However, when application to a preparation capable of being administered intramuscularly is considered, a preparation having a high concentration which is adjusted to a volume for intramuscular administration requiring a minimum volume, i.e., it is necessary to be a preparation having a concentration of 6.67 mg/ml or higher (a concentration calculated based on the assumption that the liquid amount capable for intramuscular administration is about 3 ml or less and 20 mg of famotidine, which is a single dose thereof, is contained).

JP-A-11-193233 describes a famotidine injection preparation having a pH of about 5.5 to about 7.5 which contains famotidine or its salt in an amount of about 1 mg/ml to about 40 mg/ml in terms of famotidine, especially which comprises famotidine or its salt, an acidic substance, and a water-soluble non-aqueous solvent.

The above invention using a water-soluble non-aqueous solvent is an excellent technology which solves the above problem and especially achieves a drug concentration of about 6.67 mg/ml or higher enabling intramuscular administration and a long-term stability at room temperature, but owing to the characteristic property of the water-soluble non-aqueous solvent such as polyethylene glycol, propylene glycol, or glycerin, viscosity of the formulated drug solution increases and its absorption after intramuscular administration is delayed as compared with the conventional preparation because of the factors such as the viscosity, so that the improvement has been desired.

Thus, a famotidine injection solution containing famotidine or its salt in a high concentration of from 1 to 40 mg/ml, having a good stability, and excellent in absorbability after administration, which may be capable of being administered intramuscularly, has been highly desired.

DISCLOSURE OF THE INVENTION

As a result of the extensive studies for solving the above problems, the present inventors have first found that famotidine or its salt can be unexpectedly solubilized by an water-soluble acid amide such as nicotinic acid amide, isonicotinic acid amide, or N,N-dimethylacetamide, which is hitherto not used as a solubilizing agent for famotidine preparations, in the coexistence of an acid substance such as lactic acid, the purpose being not achieved by a common solubilizing agent. Also, at the preparation of an aqueous injection solution containing famotidine or its salt, the water-soluble acid amide, and the acidic substance, they have found that famotidine can be contained in a high concentration without using a large amount of organic solvent and the stability can be assured at room temperature over a long period of time. The inventors have further found that upon the measurement of kinematic viscosity of the famotidine freeze-dried preparation containing L-aspartic acid, the famotidine injection preparation containing a water-soluble non-aqueous solvent, and the injection solution provided by the invention, no difference is observed visually but the injection solution provided by the invention has a low viscosity nearly equal to the viscosity of the freeze-dried preparation and in the famotidine injection solution, the formulation capable of avoiding absorption delay of famotidine without impairing the absorbability is enabled by controlling the kinematic viscosity of the preparation at room temperature to about 3 centistokes or less. In addition, the inventors have found that the absorbability can be further increased by preparing an injection solution wherein a sugar alcohol such as mannitol or a sugar such as glucose is contained in famotidine or its salt, the water-soluble acid amide, and the acidic substance. Based on these findings, they have accomplished the invention.

At the same time, according to the invention, since a non-aqueous solvent for the purpose of solubilization and stabilization of famotidine is entirely not used or its amount to be used can be extremely limited, it is a noteworthy effect that a pain caused by the non-aqueous solvent is not worried, necessity of adding a soothing agent including benzyl alcohol as a representative in a high concentration can be extruded, and also anxiety of absorption delay at the administration owing to a high concentration of the soothing agent, which is commonly known, can be dispelled.

Namely, the invention relates to (1) a famotidine injection solution containing famotidine or its salt in an amount of about 1 mg/ml to about 40 mg/ml in terms of the base, further containing a water-soluble acid amide in an amount of about 1 mg to about 30 mg per 1 mg of famotidine, and an acidic substance and having a pH of about 5.5 to about 7.5 and a kinematic viscosity at room temperature of about 0.9 centistokes or more to about 3 centistokes or less, (2) the famotidine injection solution, which further contains a sugar alcohol and/or sugar, (3) the famotidine injection solution, wherein a mixing amount of the sugar alcohol and/or sugar is from about 0.2 to about 16% by weight, (4) the famotidine injection solution, wherein the sugar alcohol and/or sugar is one or two or more compounds selected from the group consisting of mannitol, sorbitol, glucose, and mannose, (5) the famotidine injection solution, wherein the sugar alcohol and/or sugar is mannitol, (6) the famotidine injection solution, which contains ascorbic acid and/or erythorbic acid, (7) the famotidine injection solution, wherein the concentration of famotidine or its salt is from about 5 mg/ml to about 20 mg/ml in terms of the base, (8) the famotidine injection solution according to any one of claims 1 to 6, wherein the amount of the acidic substance to be added is from 0.2 to 20 mols relative to 1 mol of famotidine or its salt, (9) the famotidine injection solution, wherein the water-soluble acid amide is one or two or more compounds selected from the group consisting of nicotinic acid amide, isonicotinic acid amide, gentisic acid ethanolamide, urea, and N,N-dimethylacetamide, (10) the famotidine injection solution, wherein the acidic substance is one or two or more compounds selected from the group consisting of hydrochloric acid, lactic acid, L-aspartic acid, L-glutamic acid, benzoic acid, citric acid, malic acid, ascorbic acid, erythorbic acid, gluconic acid, acetic acid, and nicotinic acid, (11) the famotidine injection solution, wherein the water-soluble acid amide is one or two or more compounds selected from the group consisting of nicotinic acid amide, isonicotinic acid amide, and N,N-dimethylacetamide, and (12) the famotidine injection solution, wherein the acidic substance is lactic acid, L-aspartic acid, or L-glutamic acid.

Moreover, the invention relates to use of a water-soluble acid amide for the production of a stable famotidine injection solution. Furthermore, the invention relates to use of mannitol for the production of a stable famotidine injection solution wherein absorbability of famotidine is increased.

The "kinematic viscosity" herein is a value obtained by dividing viscosity of a liquid by its density and means a value measured using an Ubbelohde viscometer in accordance with Japanese Pharmacopoeia viscosity measuring method. In the invention, according to Japanese Pharmacopoeia, centistokes in CGS system is used as a unit. In this connection, as is apparent from the following Experimental Examples, the kinematic viscosity of the famotidine freeze-dried preparation containing L-aspartic acid is about 1 centistokes and the kinematic viscosity of the famotidine injection preparation containing a water-soluble non-aqueous solvent, which exhibits absorption delay, is about 5 centistokes. In the following, based on the above findings, the expression of a "high" viscosity in famotidine injection preparations or injection solutions means a viscosity exceeding about 3 centistokes and especially indicates about 5 centistokes which is observed in the famotidine injection preparation containing a water-soluble non-aqueous solvent, and the expression of a "low" viscosity means a viscosity of about 0.9 centistokes or more to about 3 centistokes or less.

Moreover, "famotidine or its salt in a high concentration in terms of famotidine" which is desirable in the invention means a content of famotidine of about 1 mg/ml or more, preferably about 5 mg/ml or more, most suitably about 6.67 mg/ml or more per a preparation unit.

Furthermore, "an injection solution is stable at room temperature over a long period of time" which is desirable in the invention means that the residual rate of famotidine is an acceptable limit or more (about 94% or more) even when the solution is stored at 25° C. for 1 year or more, preferably 1.5 years or more.

The injection solution of the invention will be described in more detail.

In the invention, "salt of famotidine" is not particularly limited as far as it is pharmaceutically allowable one and is a salt of famotidine capable of achieving the object of the invention in the injection solution of the invention like famotidine. Specifically, salts described in JP-B-60-56143 (or U.S. Pat. No. 4,362,736) or salts formed with acidic substances described in JP-A-11-193233 may be mentioned. These salts can be easily obtained by subjecting famotidine and the acidic substances to a conventional salt forming reaction.

In the injection solution of the invention, the concentration of famotidine or its salt is preferably from about 1 mg/ml to about 40 mg/ml, which enables administration of 20 mg of famotidine or in terms of famotidine in a volume of about 0.5 ml to about 20 ml. In the case of the concentration of about 5 mg/ml or more, the solution can be used for gentle and slow intravenous administration or intravenous infusion after dilution with a physiologically acceptable liquid such as physiological saline and, in addition, can be used for a topical administration such as intramuscular administration, subcutaneous administration, or the like.

The water-soluble acid amide for use in the invention is not particularly limited as far as it is a pharmaceutically allowable one capable of achieving the object of the invention and is a water-soluble acid amide having a group —$CONH_2$ in the molecule and an ability to solubilize famotidine or its salt. Preferably, nicotinic acid amide, isonicotinic acid amide, gentisic acid ethanolamide, urea, N,N-dimethylacetamide, and the like may be mentioned. In particular, a suitable water-soluble acid amide is nicotinic acid amide which has an experience of being used as an additive for commercially available injection solution and which is reported to have no serious harmful action. In this regard, urea is a "carbamic acid amide" as described in Japanese Pharmacopoeia and has the same function as the other water-soluble acid amides have, as one ingredient achieving solubilization, stabilization, and decrease of viscosity of the injection solution of the invention.

These water-soluble acid amides may be used singly or as a mixture of two or more of them. Furthermore, within a range imparting no serious influence on viscosity, in addition to these, water-soluble non-aqueous solvents shown in JP-A-11-193233, for example, those described in the following Table 1 may be used as auxiliary solubilizing means. As reference, kinematic viscosity of the mixed solutions of these non-aqueous solvents and water at 25° C. are shown in Table 1.

Alternatively, a pharmaceutically acceptable auxiliary solubilizing agent such as a cyclodextrin, a surfactant, or the like may be added within a range exhibiting no absorption delay.

TABLE 1

Kinematic viscosity of aqueous solutions of various non-aqueous solvents (25° C.)

| Solvent | Concentration (W/V) | | | | |
|---|---|---|---|---|---|
| | 5% | 10% | 15% | 20% | 37% |
| Polyethylene glycol 400 | 1.085 | 1.328 | 1.636 | 2.018 | 4.282 |
| Polyethylene glycol 300 | 1.076 | 1.101 | 1.539 | 1.885 | 3.707 |
| Polyethylene glycol 200 | 1.061 | 1.266 | 1.462 | 1.729 | 3.166 |
| Glycerin | 1.011 | 1.135 | 1.281 | 1.465 | 2.323 |
| Propylene glycol | 1.067 | 1.247 | 1.455 | 1.729 | 3.048 |
| Ethanol | 1.082 | 1.300 | 1.577 | 1.857 | 2.479 |

Unit: Centistokes

The amount of the above water-soluble acid amide to be added varies depending on the kind of the water-soluble acid amide and the amount of the other solubilizing auxiliary agent and is not sweepingly defined but is generally from about 1 mg to 30 mg, preferably from about 2 mg to 15 mg per 1 mg of famotidine or its salt.

The acidic substance for use in the invention is not particularly limited as far as it is a pharmaceutically allowable one capable of achieving the object of the invention and is an acidic substance having an ability to solubilize and stabilize famotidine or its salt through the formation of a salt or complex with famotidine or its salt. Preferably, hydrochloric acid, lactic acid, L-aspartic acid, L-glutamic acid, benzoic acid, citric acid, malic acid, ascorbic acid, erythorbic acid, gluconic acid, acetic acid, nicotinic acid, and the like may be mentioned. More preferred is lactic acid, L-aspartic acid, L-glutamic acid, or nicotinic acid, and further preferred is lactic acid, L-aspartic acid, or L-glutamic acid. The most suitable is lactic acid. These acidic substances may be used singly or as a mixture of two or more of them.

In addition, for the purpose of achieving an antioxidant effect of the preparation, ascorbic acid or erythorbic acid may be added. These are selected as acidic substances but also function as antioxidants.

The amount of the above acidic substance to be added varies depending on the kinds thereof, the kind of the water-soluble acid amide, adoption of the antioxidant, adoption of a buffer system, and the like, and is not sweepingly defined but is generally from about 0.2 to 20 mol, preferably from about 0.3 to 15 mol per 1 mol of famotidine or its salt.

The pH of the injection solution of the invention is preferably about 5.5 to about 7.5, more preferably from about 5.5 to about 7.0. It is preferable to mix an acidic substance so that the pH of the injection solution of the invention is finally adjusted to the above range or to adjust the pH to the above range with a basic substance such as sodium hydroxide after mixing an excess of the acidic substance.

The kinematic viscosity of the injection solution of the invention at room temperature is preferably from about 0.9 centistokes or more to about 3 centistokes or less, more preferably from about 0.9 centistokes or more to about 2 centistokes or less, most suitably from about 0.9 centistokes or more to about 1 centistokes or less.

In order to enhance the absorbability at intramuscular administration, in addition to the water-soluble acid amide and the acidic substance, a sugar alcohol or sugar can be added. The sugar alcohol or sugar is preferably mannitol, sorbitol, glucose, or mannose, and more preferably mannitol. These sugar alcohol and sugar may be used in combination. The mixing amount in the case that the sugar alcohol or sugar is added varies depending on the kind of the other ingredients and their mixing amounts, but is preferably from about 0.2 to about 16% by weight, more preferably from about 1 to about 10% by weight.

In the injection solution of the invention, within a range without impairing the object of the invention, additives including a soothing agent such as benzyl alcohol, mepivacaine hydrochloride, or xylocaine hydrochloride, an antiseptic such as methyl parabenzoate, propyl parabenzoate, thimerosal, or chlorobutanol, and the like, can be added if necessary. Moreover, for alleviating local toxicity, a hydrophilic low-molecular-weight additive such as sodium chloride can be added, if necessary.

The injection solution of the invention is excellent in mixing ability with a sodium chloride injection solution such as physiological saline, a sugar infusion solution, an electrolyte infusion solution, and the other infusion solutions, and thus can be used in combination with these infusion solutions.

The following will describe a process for producing the injection solution of the invention.

In the steps for producing the injection solution of the invention, for example, water for injection is added to famotidine or its salt and a water-soluble acid amide, and further an acidic substance is added thereto to dissolve famotidine or its salt.

In consideration of compatibility with water for injection, the water-soluble acid amide, and the acidic substance, mannitol and the other additives are added at a suitable step of the above production process and dissolved. Then, the thus obtained injection solution is sterilized and dispensed into containers for injection including ampoules and others, and the containers are sealed and packaged.

The injection solution of the invention can be sterilized by any of known methods, but in order to reduce the decrease of content of famotidine during the preparation as far as possible, it is preferable to produce the solution by a known aseptic manipulation other than sterilization by heating, for example, sterile filtration described in Examples or the like. Furthermore, the product may be treated so that it does not come into contact with oxygen by blowing nitrogen gas into a prepared solution or filling a headspace of an ampoule with nitrogen gas. Moreover, for the purpose of preventing photodecomposition of the drug during the production, the operation may be carried out in a dark place.

BEST MODE FOR CARRYING OUT THE INVENTION

Figure 1:
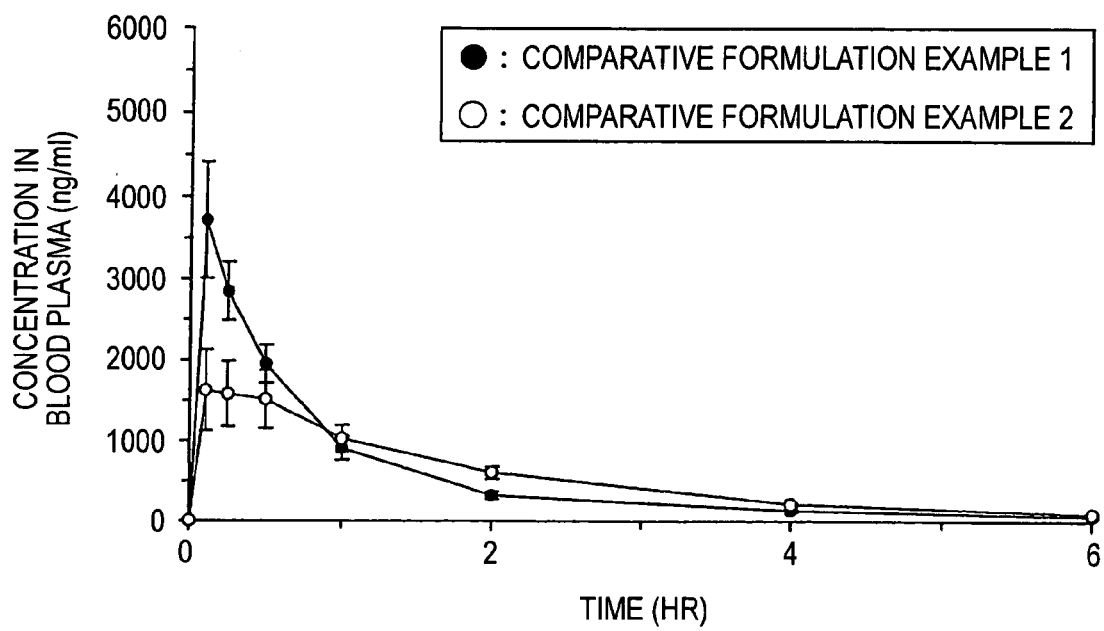
FIG. 1 is a graph illustrating a concentration change of Comparative Formulation 2 and Comparative Formulation 1 in blood plasma.

By preparing a famotidine injection solution containing famotidine or its salt in an amount of about 1 mg/ml to about 40 mg/ml in terms of the base and having a pH of about 5.5 to about 7.5 and a kinematic viscosity at room temperature of about 0.9 centistokes or more to about 3 centistokes or less or by preparing an injection solution containing famotidine or its salt, a water-soluble acid amide, and an acidic substance, the invention exhibits a remarkable effect of enabling provision of a low-viscosity famotidine stabilized injection solution containing famotidine at a high concentration, being stable over a long period of time at room temperature, and never deteriorating the absorption of famotidine which can be hardly provided so far.

Moreover, the invention of a famotidine stabilized injection solution mixed with a sugar alcohol or sugar in addition to famotidine or its salt, the water-soluble acid amide, and the acidic substance is useful since it enables further increase of the absorbability to a level equal to that of a freeze-dried injection preparation.

These effects are confirmed by the following Experimental Examples.

EXPERIMENTAL EXAMPLES

Comparative Formulation 1

Commercially Available Famotidine Injection Preparation (Freeze-dried Preparation)

The preparation was prepared by reconstituting a commercially available famotidine injection preparation (freeze-dried preparation) with water for injection so that the concentration of famotidine becomes 10 mg/ml.

Comparative Formulation 2

Famotidine Injection Preparation Containing a Water-soluble Non-aqueous Solvent In accordance with Example 1 of JP-A-11-193233, an injection solution having formulation of pH 6.4 containing 10 mg/ml of famotidine, 370 mg/ml of polyethylene glycol 400, 20 mg/ml of benzyl alcohol, and 1.8 mg/ml of lactic acid was prepared.

In this connection, the pH of the injection solution was measured in accordance with the pH measuring method described in General Test Methods of Japanese Pharmacopoeia. The pH of each injection solution of the following Examples was described in each Example.

Experimental Method 1 Measurement of Kinematic Viscosity

The viscosity of each injection solution of the following Examples 1 to 6 and 8 and Comparative Formulations 1 and 2 was measured in accordance with the viscosity measuring method using an Ubbelohde viscometer described in General Test Methods of Japanese Pharmacopoeia.

Experimental Results

The kinematic viscosity of each injection solution of the following Examples 1 to 6 and 8 to 13 was described in each Example.

On the other hand, the kinematic viscosity of the commercial famotidine injection preparation (freeze-dried preparation) [Comparative Formulation 1] and that of the famotidine injection preparation containing a water-soluble non-aqueous solvent [Comparative Formulation 2] were about 1 centistokes and about 5 centistokes, respectively.

As a result, it was confirmed that the kinematic viscosity of Comparative Formulation 2, i.e., a famotidine injection preparation mixed with a water-soluble non-aqueous solvent was extremely higher than that of Comparative Formulation 1, i.e., a freeze-dried injection preparation.

Experimental Method 2 Test of Administering Comparative Formulations 1 and 2 to Rabbits Each injection solution of Comparative Formulations 1 and 2 was intramuscularly administered to a hind limb part of rabbits (n=5) according to a cross-over method. Blood was collected with time and the drug concentration in blood plasma was measured by LC-MS/MS method.

Experimental Results

The pharmacokinetic parameters of Comparative Formulations 1 and 2 were C max 3506.9±315.5 ng/mL, T max 0.1±0.1 hr, and MRT 1.1±0.1 hr (n=5) and C max 1684.5±385.3 ng/mL, T max 0.4±0.1 hr, and MRT 1.6±0.2 hr (n=5), respectively (cf. FIG. 1). As a result, in the injection preparation of Comparative Formulation 2, C max was ½ or less, T max was 4 times, and MRT was extended as compared with the case of the commercially available freeze-dried injection preparation, and hence the absorption was considered to be drastically delayed.

Experimental Method 3 Test of Administering Each Example to Rabbits

Each of the injection solutions of Examples 3, 4, 6, 9, 10 to 13, and 19 and the injection solution of Comparative Formulation 1 were intramuscularly administered to a hind limb part of the same rabbits. Also, each of the injection solutions of Examples 17 and 18 and the injection solution of Example 19 were intramuscularly administered to a hind limb part of the same rabbits. Blood was collected with time and the drug concentration in blood plasma was measured by HPLC/UV method.

Experimental Results

The pharmacokinetic parameters in the case that the drug solution of Example 3 was intramuscularly administered to a hind limb part of rabbits were C max 2973.6±755.6 ng/mL, T max 0.2±0.1 hr, and MRT 1.4±0.1 hr (n=8) and the pharmacokinetic parameters of the solution obtained by reconstituting the commercially available freeze-dried preparation with water for injection and administered by the cross-over method were C max 3904.1±1168.6 ng/mL, T max 0.2±0.1 hr, and MRT 1.1±0.1 hr (n=8).

The pharmacokinetic parameters in the case that the drug solution of Example 4 was intramuscularly administered to a hind limb part of rabbits were C max 3736.9±1155.0 ng/mL, T max 0.2±0.1 hr, and MRT 1.2±0.1 hr (n=8) and the pharmacokinetic parameters of the solution obtained by reconstituting the commercially available freeze-dried preparation with water for injection and administered by the cross-over method were C max 5281.0±1908.3 ng/mL, T max 0.1±0.1 hr, and MRT 1.1±0.1 hr (n=8).

The pharmacokinetic parameters in the case that the drug solution of Example 6 was intramuscularly administered to a hind limb part of rabbits were C max 3940.2±927.9 ng/mL, T max 0.2±0.2 hr, and MRT 1.1±0.1 hr (n=6) and the pharmacokinetic parameters of the solution obtained by reconstituting the commercially available freeze-dried preparation with water for injection and administered by the cross-over method were C max 5114.4±1359.7 ng/mL, T max 0.2±0.2 hr, and MRT 1.0±0.1 hr (n=6).

Figure 2:
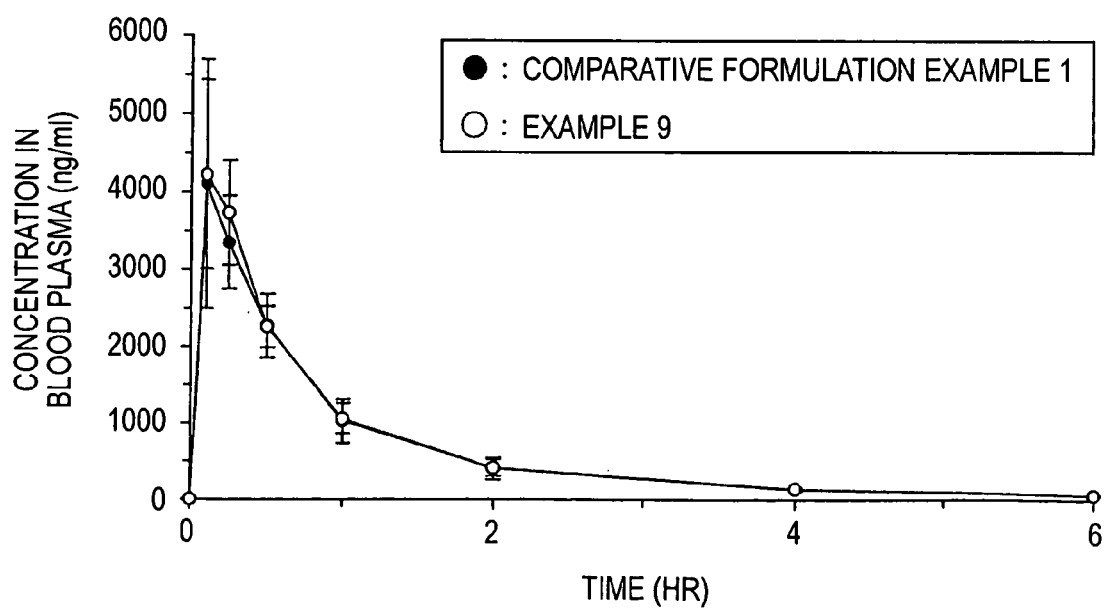
FIG. 2 is a graph illustrating a concentration change of Example 9 and Comparative Formulation 1 in blood plasma.

The pharmacokinetic parameters in the case that the drug solution of Example 9 was intramuscularly administered to a hind limb part of rabbits were C max 4356.4±1075.4 ng/mL, T max 0.1±0.1 hr, and MRT 1.1±0.1 hr (n=10) and the pharmacokinetic parameters of the solution obtained by reconstituting the commercially available freeze-dried preparation with water for injection and administered by the cross-over method were C max 4328.1±1276.1 ng/mL, T max 0.2±0.1 hr, and MRT 1.1±0.2 hr (n=10) (cf. FIG. 2).

Figure 3:
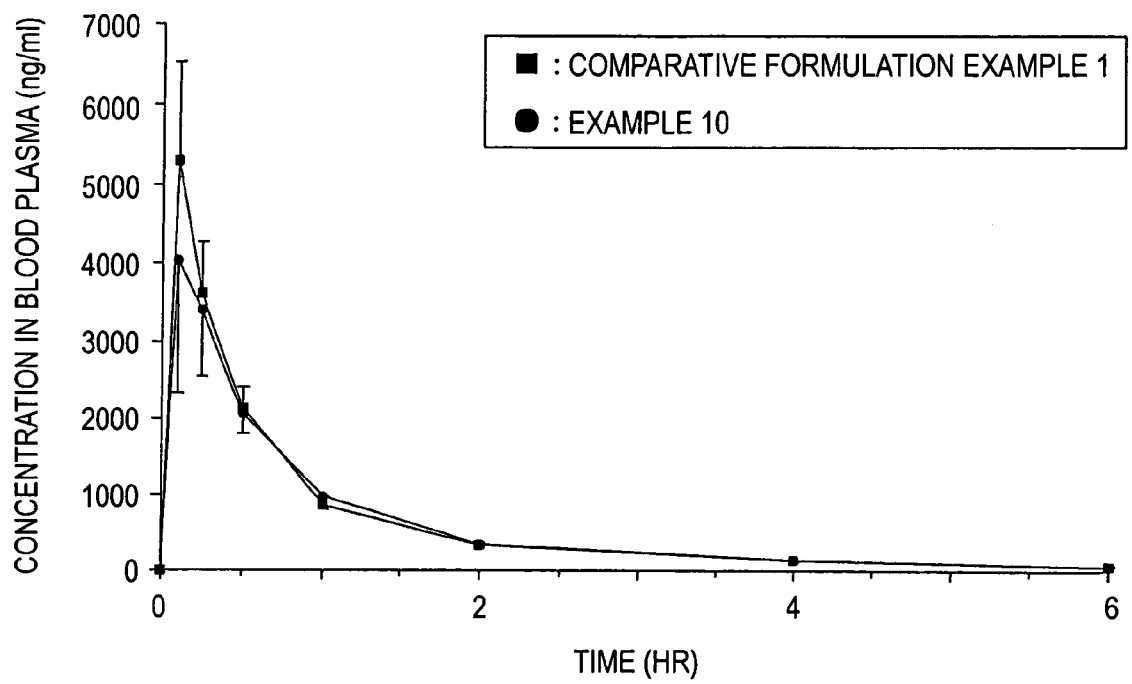
FIG. 3 is a graph illustrating a concentration change of Example 10 and Comparative Formulation 1 in blood plasma.

The pharmacokinetic parameters in the case that the drug solution of Example 10 was intramuscularly administered to a hind limb part of rabbits were C max 4290.9±1425.6 ng/mL, T max 0.1±0.1 hr, and MRT 1.1±0.1 hr (n=6) and the pharmacokinetic parameters of the solution obtained by reconstituting the commercially available freeze-dried preparation with water for injection and administered by the cross-over method were C max 5299.3±1230.6 ng/mL, T max 0.1±0.0 hr, and MRT 1.0±0.1 hr (n=6) (cf. FIG. 3).

Figure 4:
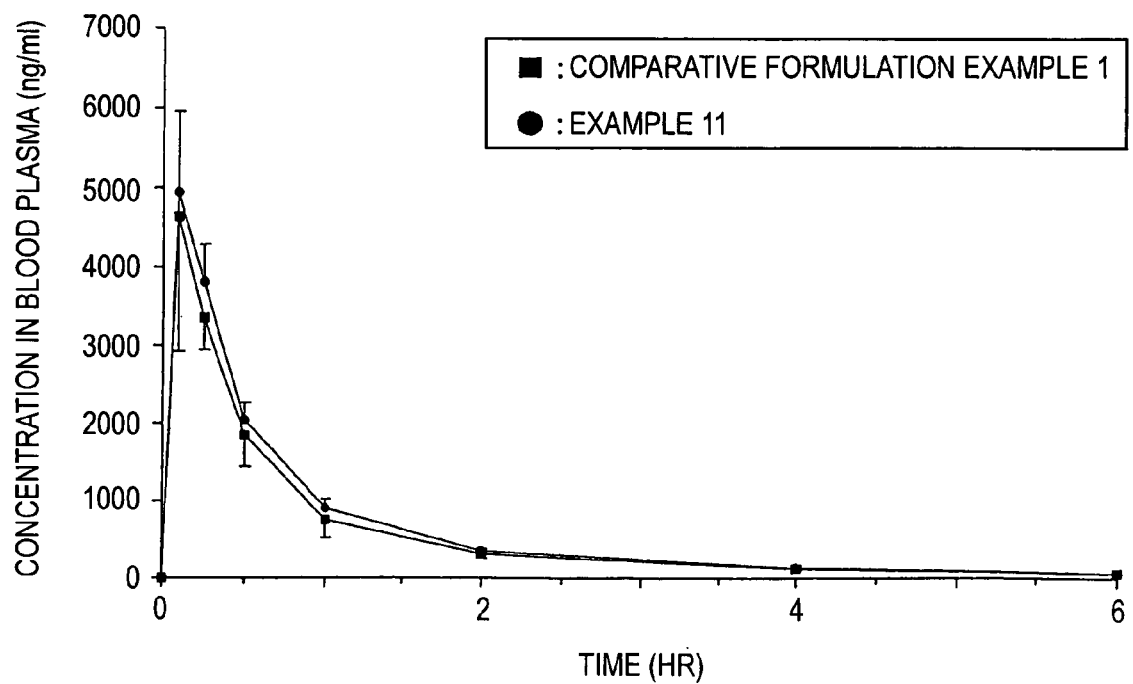
FIG. 4 is a graph illustrating a concentration change of Example 11 and Comparative Formulation 1 in blood plasma.

The pharmacokinetic parameters in the case that the drug solution of Example 11 was intramuscularly administered to a hind limb part of rabbits were C max 4935.2±1027.8 ng/mL, T max 0.1±0.0 hr, and MRT 1.0±0.0 hr (n=6) and the pharmacokinetic parameters of the solution obtained by reconstituting the commercially available freeze-dried preparation with water for injection and administered by the cross-over method were C max 4794.4±1412.4 ng/mL, T max 0.1±0.1 hr, and MRT 1.0±0.1 hr (n=6) (cf. FIG. 4).

Figure 5:
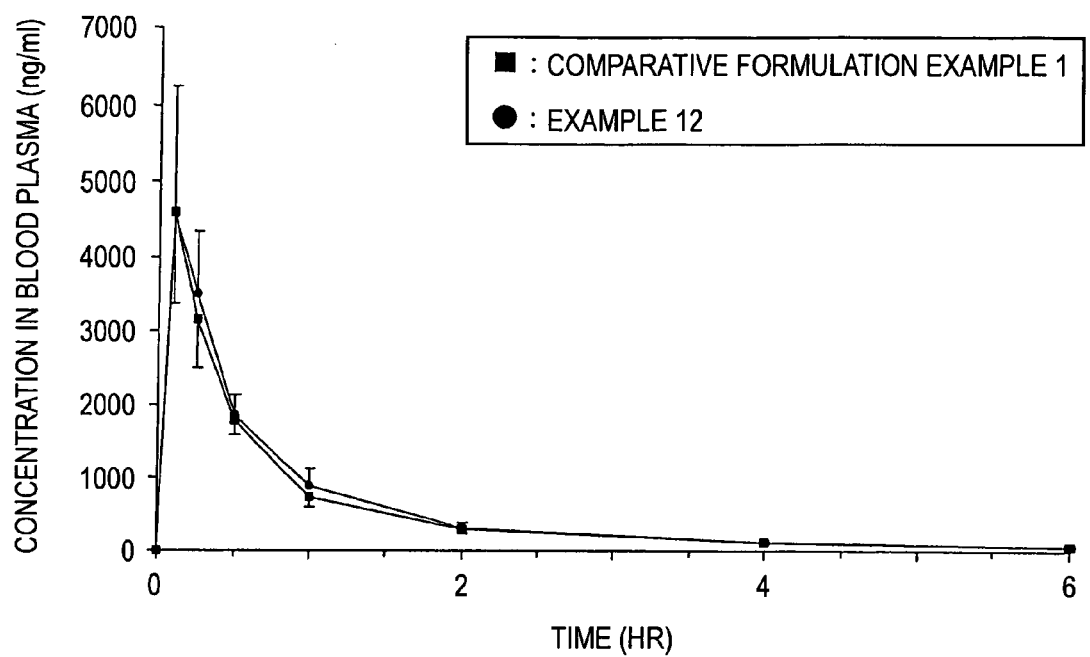
FIG. 5 is a graph illustrating a concentration change of Example 12 and Comparative Formulation 1 in blood plasma.

The pharmacokinetic parameters in the case that the drug solution of Example 12 was intramuscularly administered to a hind limb part of rabbits were C max 4711.4±1421.2 ng/mL, T max 0.1±0.1 hr, and MRT 1.0±0.1 hr (n=6) and the pharmacokinetic parameters of the solution obtained by reconstituting the commercially available freeze-dried preparation with water for injection and administered by the cross-over method were C max 4601.8±1236.6 ng/mL, T max 0.1±0.0 hr, and MRT 1.0±0.1 hr (n=6) (cf. FIG. 5).

Figure 6:
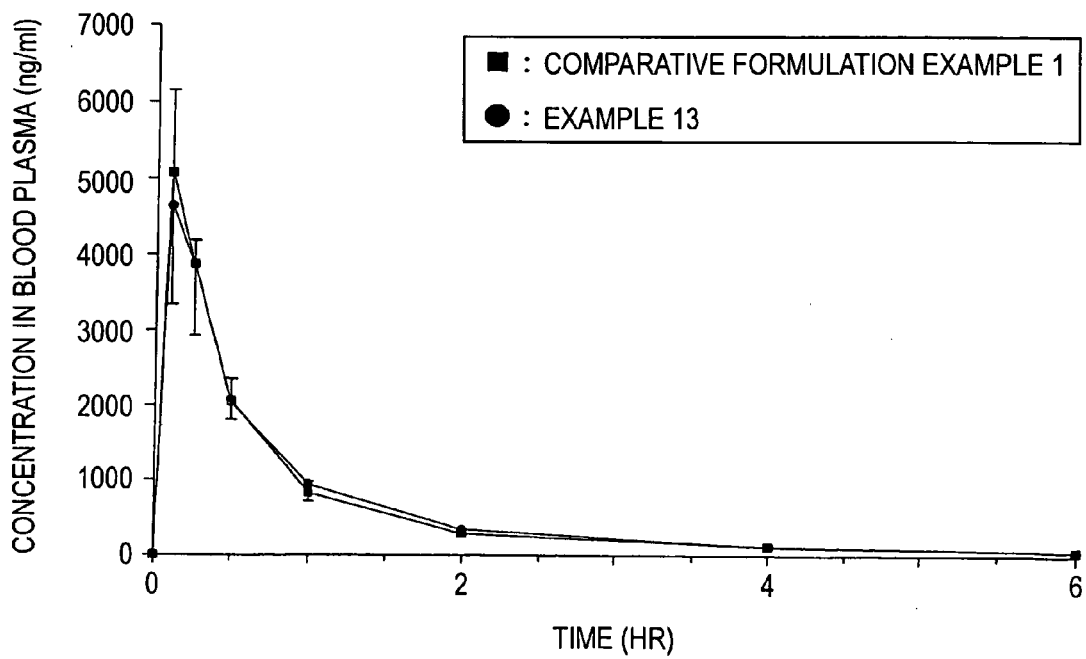
FIG. 6 is a graph illustrating a concentration change of Example 13 and Comparative Formulation 1 in blood plasma.

The pharmacokinetic parameters in the case that, the drug solution of Example 13 was intramuscularly administered to a hind limb part of rabbits were C max 4642.9±1301.9 ng/mL, T max 0.1±0.0 hr, and MRT 1.0±0.1 hr (n=6) and the pharmacokinetic parameters of the solution obtained by reconstituting the commercially available freeze-dried preparation with water for injection and administered by the cross-over method were C max 5164.5±909.4 ng/mL, T max 0.1±0.1 hr, and MRT 0.9±0.1 hr (n=6) (cf. FIG. 6).

The pharmacokinetic parameters in the case that the drug solution of Example 17 was intramuscularly administered to a hind limb part of rabbits were C max 4197.5±1278.8 ng/mL, T max 0.1±0.0 hr, and MRT 1.2±0.1 hr (n=6) and the pharmacokinetic parameters in the case that the drug solution of Example 9 was intramuscularly administered to a hind limb part of the same rabbits were C max 4804.3±1301.4 ng/mL, T max 0.1±0.0 hr, and MRT 1.1±0.1 hr (n=6).

The pharmacokinetic parameters in the case that the drug solution of Example 18 was intramuscularly administered to a hind limb part of rabbits were C max 4985.7±433.2 ng/mL, T max 0.1±0.1 hr, and MRT 1.0±0.1 hr (n=6) and the pharmacokinetic parameters in the case that the drug solution of Example 9 was intramuscularly administered to a hind limb part of the same rabbits were C max 5017.2±1159.8 ng/mL, T max 0.1±0.1 hr, and MRT 1.0±0.1 hr (n=6).

The pharmacokinetic parameters in the case that the drug solution of Example 19 was intramuscularly administered to a hind limb part of rabbits were C max 5000.6±1091.6 ng/mL, T max 0.1±0.1 hr, and MRT 1.1±0.1 hr (n=6) and the pharmacokinetic parameters of the solution obtained by reconstituting the commercially available freeze-dried preparation in water for injection and administered by the cross-over method were C max 5590.0±1348.0 ng/mL, T max 0.1±0.1 hr, and MRT 1.0±0.1 hr (n=6).

As a result, it was confirmed that each of the injection solutions of Examples 3, 4, 6, 9, 10, 11, 12, 13, 17, 18, and 19 exhibited absorbability similar to that of the commercially available freeze-dried injection preparation.

Experimental Method 4

With regard to the stability of the injection solutions prepared in Examples 1, 2, 4, and 10 to 15, the residual rates of famotidine were measured after storage under a condition of 50° C. for 1 month and/or under a condition of 40° C. for 3 months.

Experimental Results

The residual rates of famotidine after storage of the preparation of Example 1 under a condition of 50° C. for 1 month and under a condition of 40° C. for 3 months were 96.7% and 96.3%, respectively.

The residual rates of famotidine after storage of the preparation of Example 2 under a condition of 50° C. for 1 month and under a condition of 40° C. for 3 months were 96.3% and 96.1%, respectively.

The residual rate of famotidine after storage of the preparation of Example 4 under a condition of 50° C. for 1 month was 96.1%.

The residual rate of famotidine after storage of the preparation of Example 9 under a condition of 40° C. for 3 months was 96.0%.

The residual rate of famotidine after storage of the preparation of Example 10 under a condition of 40° C. for 3 months was 97.2%.

The residual rate of famotidine after storage of the preparation of Example 11 under a condition of 40° C. for 3 months was 96.4%.

The residual rate of famotidine after storage of the preparation of Example 12 under a condition of 40° C. for 3 months was 95.7%.

The residual rate of famotidine after storage of the preparation of Example 13 under a condition of 40° C. for 3 months was 95.2%.

The residual rate of famotidine after storage of the preparation of Example 14 under a condition of 50° C. for 1 month was 94.7%.

The residual rate of famotidine after storage of the preparation of Example 15 under a condition of 50° C. for 1 month was 95.9%.

Consideration

As is apparent from the above Experimental Examples, it has been confirmed that the famotidine injection preparation of Comparative Formulation 2 mixed with a water-soluble non-aqueous solvent has a high kinematic viscosity and exhibits a delayed absorption of famotidine as compared with Comparative Formulation 1 which is a commercially available famotidine freeze-dried injection preparation, while the famotidine injection solution of the invention can be prepared within the pH range of about 5.5 to about 7.5, exhibits absorbability similar to that of Comparative Formulation 1 which is a freeze-dried injection preparation, and is stable over a long period of time, kinematic viscosity is desirably set at about 0.9 centistokes or more to about 3 centistokes or less, preferably about 0.9 centistokes or more to about 2 centistokes or less, most suitably about 0.9 centistokes or more to about 1 centistokes or less in order to exhibit absorbability similar to that of the commercially available freeze-dried injection preparation, and the delayed drug absorption of the famotidine injection preparation mixed with a water-soluble non-aqueous solvent such as polyethylene glycol (macrogol) is mainly caused by a high kinematic viscosity of the preparation.

EXAMPLES

The following will specifically describe the invention with reference to Examples, but the scope of the invention is not limited thereby.

Example 1

10 mg/ml Injection Solution Containing Nicotinic Acid Amide (10%)+Lactic Acid; Containing Benzyl Alcohol To 10 g of famotidine and 100 g of nicotinic acid amide were added about 800 ml of water for injection and 19 ml of a 100 mg/ml aqueous lactic acid solution, followed by stirring to dissolve them. After complete dissolution of famotidine, 9 g of benzyl alcohol was added thereto and water for injection was further added to make the total volume 1000 ml, whereby an injection solution having a pH of 6.4 and a kinematic viscosity at room temperature of 1.09 centistokes was obtained.

After sterile filtration by a usual manner, the solution was charged into an ampoule and after the headspace was replaced with nitrogen, the ampoule was sealed with melting to prepare an injectable product.

Example 2

10 mg/ml Injection Solution Containing Nicotinic Acid Amide (5%)+Lactic Acid; Containing Benzyl Alcohol To 10 g of famotidine and 50 g of nicotinic acid amide were added about 800 ml of water for injection and 22 ml of a 100 mg/ml aqueous lactic acid solution, followed by stirring to dissolve them. After complete dissolution of famotidine, 9 g of benzyl alcohol was added thereto and water for injection was further added to make the total volume 1000 ml, whereby an injection solution having a pH of 6.2 and a kinematic viscosity at room temperature of 1.00 centistokes was obtained.

After sterile filtration by a usual manner, the solution was charged into an ampoule and after the headspace was replaced with nitrogen, the ampoule was sealed with melting to prepare an injectable product.

Example 3

10 mg/ml Injection Solution Containing Nicotinic Acid Amide (10%)+Lactic Acid; No Benzyl Alcohol To 1 g of famotidine and 10 g of nicotinic acid amide were added about 40 ml of water for injection and 20 ml of a 10 mg/ml aqueous lactic acid solution, followed by stirring to dissolve them. After complete dissolution of famotidine, water for injection was added to make the total volume 100 ml, whereby an injection solution having a pH of 6.4 and a kinematic viscosity at room temperature of 1.12 centistokes was obtained.

Example 4

10 mg/ml Injection Solution Containing Nicotinic Acid Amide (10%)+Aspartic Acid; No Benzyl Alcohol To 5 g of famotidine, 1.478 g of L-aspartic acid, and 50 g of nicotinic acid amide was added water for injection to make the volume about 450 ml, followed by stirring to dissolve them. After complete dissolution of famotidine, water for injection was added to make the total volume 500 ml, whereby an injection solution having a pH of 6.4 was obtained.

After sterile filtration by a usual manner, the solution was charged into an ampoule and after the headspace was replaced with nitrogen, the ampoule was sealed with melting to prepare an injectable product.

Example 5

10 mg/ml Injection Solution Containing Nicotinic Acid Amide (5%)+Propylene Glycol+Lactic Acid; Containing Benzyl Alcohol To 1 g of famotidine and 5 g of nicotinic acid amide were added about 80 ml of water for injection and 1.90 ml of a 100 mg/ml aqueous lactic acid solution, and 5 g of propylene glycol and 2 g of benzyl alcohol were further added thereto, followed by stirring to dissolve them. After complete dissolution of famotidine, water for injection was added to make the total volume 100 ml, whereby an injection solution having a pH of 6.4 and a kinematic viscosity at room temperature of 1.17 centistokes was obtained.

Example 6

10 mg/ml Injection Solution Containing Nicotinic Acid Amide (5%)+Lactic Acid

To 5 g of famotidine and 25 g of nicotinic acid amide were added about 420 ml of water for injection and 11.0 ml of a 100 mg/ml aqueous lactic acid solution, followed by stirring to dissolve them. After complete dissolution of famotidine, water for injection was added to make the total volume 500 ml, whereby an injection solution having a pH of 6.2 and a kinematic viscosity at room temperature of 1.01 centistokes was obtained.

Example 7

20 mg/ml Injection Solution Containing N,N-dimethylacetamide+Lactic Acid; Containing Benzyl Alcohol To 2 g of famotidine was added 20 g of N,N-dimethylacetamide to form a solution, to which about 60 ml of water for injection was added. Thereto were added 3.58 ml of a 100 mg/ml aqueous lactic acid solution and 0.9 g of benzyl alcohol, and the whole was stirred. Then, water for injection was added to make the total volume 100 ml, whereby an injection solution having a pH of 6.2 was obtained.

After sterile filtration by a usual manner, the solution was charged into an ampoule and after the headspace was replaced with nitrogen, the ampoule was sealed with melting to prepare an injectable product.

Example 8

10 mg/ml Injection Solution Containing Isonicotinic Acid Amide+Lactic Acid

To 1 g of famotidine and 5 g of isonicotinic acid amide were added about 80 ml of water for injection and 2.20 ml of a 100 mg/ml aqueous lactic acid solution, followed by stirring to dissolve them. After complete dissolution of famotidine, water for injection was added to make the total volume 100 ml, whereby an injection solution having a pH of 6.2 and a kinematic viscosity at room temperature of 0.95 centistokes was obtained.

Example 9

10 mg/ml Injection Solution Containing Nicotinic Acid Amide (5%)+Lactic Acid; Containing Mannitol (2%)

To 10 g of famotidine, 50 g of nicotinic acid amide, and 20 g of mannitol were added about 800 ml of water for injection and 22 ml of a 100 mg/ml aqueous lactic acid solution, followed by stirring to dissolve them. After complete dissolution of famotidine, water for injection was further added to make the total volume 1000 ml, whereby an injection solution having a pH of 6.1 and a kinematic viscosity at room temperature of 1.07 centistokes was obtained.

After sterile filtration by a usual manner, the solution was charged into an ampoule and after the headspace was replaced with nitrogen, the ampoule was sealed with melting to prepare an injectable product.

Example 10

10 mg/ml Injection Solution Containing Nicotinic Acid Amide (5%)+Lactic Acid; Containing Mannitol (2%) (Non-buffer System, pH 6.2)

To 10 g of famotidine, 50 g of nicotinic acid amide, and 20 g of mannitol were added about 800 ml of water for injection and 17 ml of a 100 mg/ml aqueous lactic acid solution, followed by stirring to dissolve them. After complete dissolution of famotidine, 1 g of ascorbic acid was added and dissolved under blowing nitrogen gas into the drug solution and water for injection was further added to make the total volume 1000 ml, whereby an injection solution having a pH of 6.2 and a kinematic viscosity at room temperature of 1.08 centistokes was obtained.

After sterile filtration by a usual manner, the solution was charged into an ampoule and after the headspace was replaced with nitrogen, the ampoule was sealed with melting to prepare an injectable product.

Example 11

10 mg/ml Injection Solution Containing Nicotinic Acid Amide (5%)+Lactic Acid; Containing Mannitol (2%) (Non-buffer System, pH 5.8)

To 10 g of famotidine, 50 g of nicotinic acid amide, and 20 g of mannitol were added about 800 ml of water for injection and 20 ml of a 100 mg/ml aqueous lactic acid solution, followed by stirring to dissolve them. After complete dissolution of famotidine, 1 g of ascorbic acid was added and dissolved under blowing nitrogen gas into the drug solution and water for injection was further added to make the total volume 1000 ml, whereby an injection solution having a pH of 5.8 and a kinematic viscosity at room temperature of 1.07 centistokes was obtained.

After sterile filtration by a usual manner, the solution was charged into an ampoule and after the headspace was replaced with nitrogen, the ampoule was sealed with melting to prepare an injectable product.

Example 12

10 mg/ml Injection Solution Containing Nicotinic Acid Amide (5%)+Lactic Acid; Containing Mannitol (2%) (Buffer System, pH 6.2)

To 10 g of famotidine, 50 g of nicotinic acid amide, and 20 g of mannitol were added about 750 ml of water for injection, 61 ml of a 100 mg/ml aqueous lactic acid solution, and 30 ml of a 1N sodium hydroxide solution, followed by stirring to dissolve them. After complete dissolution of famotidine, 1 g of ascorbic acid was added and dissolved under blowing nitrogen gas into the drug solution and a suitable amount of a 1N sodium hydroxide solution was added to make the pH 6.1. Water for injection was further added to make the total volume 1000 ml, whereby an injection solution having a pH of 6.2 and a kinematic viscosity at room temperature of 1.09 centistokes was obtained.

After sterile filtration by a usual manner, the solution was charged into an ampoule and after the headspace was replaced with nitrogen, the ampoule was sealed with melting to prepare an injectable product.

Example 13

10 mg/ml Injection Solution Containing Nicotinic Acid Amide (5%)+Lactic Acid; Containing Mannitol (2%) (Buffer System, pH 5.8)

To 10 g of famotidine, 50 g of nicotinic acid amide, and 20 g of mannitol were added about 750 ml of water for injection, 70 ml of a 100 mg/ml aqueous lactic acid solution, and 30 ml of a 1N sodium hydroxide solution, followed by stirring to dissolve them. After complete dissolution of famotidine, 1 g of ascorbic acid was added and dissolved under blowing nitrogen gas into the drug solution and a suitable amount of a 1N sodium hydroxide solution was added to make the pH 5.8. Water for injection was further added to make the total volume 1000 ml, whereby an injection solution having a pH of 5.8 and a kinematic viscosity at room temperature of 1.09 centistokes was obtained.

After sterile filtration by a usual manner, the solution was charged into an ampoule and after the headspace was replaced with nitrogen, the ampoule was sealed with melting to prepare an injectable product.

Example 14

10 mg/ml Injection Solution Containing Nicotinic Acid Amide (5%)+Citric Acid; Containing Mannitol (2%)

To 10 g of famotidine, 50 g of nicotinic acid amide, 2.07 g of citric acid monohydrate, and 20 g of mannitol was added about 800 ml of water for injection, followed by stirring to dissolve them. After complete dissolution of famotidine, water for injection was further added to make the total volume 1000 ml, whereby an injection solution having a pH of 6.1 was obtained.

After sterile filtration by a usual manner, the solution was charged into an ampoule and after the headspace was replaced with nitrogen, the ampoule was sealed with melting to prepare an injectable product.

Example 15

10 mg/ml Injection Solution Containing Nicotinic Acid Amide (5%)+Citric Acid; Containing Mannitol (2%) and Ascorbic Acid (0.1%)

To 10 g of famotidine, 50 g of nicotinic acid amide, 1.60 g of citric acid monohydrate, and 20 g of mannitol was added about 800 ml of water for injection, followed by stirring to dissolve them. After complete dissolution of famotidine, 1 g of ascorbic acid was added and dissolved under blowing nitrogen gas into the drug solution and water for injection was further added to make the total volume 1000 ml, whereby an injection solution having a pH of 6.1 was obtained.

After sterile filtration by a usual manner, the solution was charged into an ampoule and after the headspace was replaced with nitrogen, the ampoule was sealed with melting to prepare an injectable product.

Example 16

10 mg/ml Injection Solution Containing Nicotinic Acid Amide (5%)+Lactic Acid; Containing Mannitol (2%) and Erythorbic Acid (0.1%)

To 2 g of famotidine, 10 g of nicotinic acid amide, and 4 g of mannitol were added about 150 ml of water for injection and 22 ml of a 100 mg/ml aqueous lactic acid solution, followed by stirring to dissolve them. Then, a suitable amount of a 1N sodium hydroxide solution was added to make the pH 6.2. After complete dissolution of famotidine, 0.2 g of erythorbic acid was added and dissolved and water for injection was further added to make the total volume 1000 ml, whereby an injection solution having a pH of 6.2 was obtained.

After sterile filtration by a usual manner, the solution was charged into an ampoule and after the headspace was replaced with nitrogen, the ampoule was sealed with melting to prepare an injectable product.

When the solution was stored under a condition of 60° C. for 1 week, the resulting profile of the decomposed product was equal to the profile of the decomposed product of the preparation wherein ascorbic acid was added instead of erythorbic acid as a reference.

Example 17

10 mg/ml Injection Solution Containing Nicotinic Acid Amide (5%)+Lactic Acid; Containing Glucose (2%)

To 2 g of famotidine, 10 g of nicotinic acid amide, and 4 g of glucose were added about 160 ml of water for injection and 4.4 ml of a 100 mg/ml aqueous lactic acid solution, followed by stirring to dissolve them. After complete dissolution of famotidine, water for injection was further added to make the total volume 200 ml, whereby an injection solution having a pH of 6.1 was obtained.

After sterile filtration by a usual manner, the solution was charged into an ampoule and after the headspace was replaced with nitrogen, the ampoule was sealed with melting to prepare an injectable product.

Example 18

10 mg/ml Injection Solution Containing Nicotinic Acid Amide (5%)+Lactic Acid; Containing Mannose (2%)

To 2 g of famotidine, 10 g of nicotinic acid amide, and 4 g of mannose were added about 160 ml of water for injection and 4.4 ml of a 100 mg/ml aqueous lactic acid solution, followed by stirring to dissolve them. After complete dissolution of famotidine, water for injection was further added to make the total volume 200 ml, whereby an injection solution having a pH of 6.1 was obtained.

After sterile filtration by a usual manner, the solution was charged into an ampoule and after the headspace was replaced with nitrogen, the ampoule was sealed with melting to prepare an injectable product.

Example 19

10 mg/ml Injection Solution Containing Nicotinic Acid Amide (5%)+Lactic Acid; Containing Sorbitol (5%)

To 2 g of famotidine, 10 g of nicotinic acid amide, and 10 g of sorbitol were added about 160 ml of water for injection and 4.4 ml of a 100 mg/ml aqueous lactic acid solution, followed by stirring to dissolve them. After complete dissolution of famotidine, water for injection was further added to make the total volume 200 ml, whereby an injection solution having a pH of 6.1 was obtained.

After sterile filtration by a usual manner, the solution was charged into an ampoule and after the headspace was replaced with nitrogen, the ampoule was sealed with melting to prepare an injectable product.

INDUSTRIAL APPLICABILITY

By preparing a famotidine injection solution containing famotidine or its salt in an amount of about 1 mg/ml to about 40 mg/ml in terms of the base and having a pH of about 5.5 to about 7.5 and a kinematic viscosity at room temperature of about 0.9 centistokes or more to about 3 centistokes or less or by preparing an injection solution containing famotidine or its salt, a water-soluble acid amide and an acidic substance, the invention exhibits a remarkable effect of enabling provision of a low-viscosity famotidine injection solution containing famotidine at a high concentration, being stable over a long period of time at room temperature, and never deteriorating the absorption of famotidine, which can be hardly provided so far.

Moreover, the invention of a famotidine injection solution mixed with a sugar alcohol or sugar in addition to famotidine or its salt, the water-soluble acid amide, and the acidic substance is useful since it enables further increase of the absorbability to the extent equal to that of a freeze-dried injection preparation.

The invention claimed is:

1. A famotidine injection solution containing famotidine or its salt in an amount of about 1 mg/ml to about 40 mg/ml in terms of the base, further containing one or two or more water-soluble acid amides selected from the group consisting of nicotinic acid amide, isonicotinic acid amide, gentisic acid ethanolamide, urea and N,N-dimethylacetamide in an amount of about 1 mg to about 30 mg per 1 mg of famotidine, and an acidic substance, and having a pH of about 5.5 to about 7.5 and a kinematic viscosity at room temperature of about 0.9 centistokes or more to about 3 centistokes or less.

2. The famotidine injection solution according to claim 1, which further contains a sugar alcohol and/or sugar.

3. The famotidine injection solution according to claim 2, wherein a mixing amount of the sugar alcohol and/or sugar is from about 0.2 to about 16% by weight.

4. The famotidine injection solution according to claim 2, wherein the sugar alcohol and/or sugar is one or two or more compounds selected from the group consisting of mannitol, sorbitol, glucose, and mannose.

5. The famotidine injection solution according to claim 2, wherein the sugar alcohol and/or sugar is mannitol.

6. The famotidine injection solution according to claim 1, which further contains ascorbic acid and/or erythorbic acid.

7. The famotidine injection solution according to claim 1, wherein the concentration of famotidine or its salt is from about 5 mg/ml to about 20 mg/ml in terms of the base.

8. The famotidine injection solution according to claim 1, wherein the amount of the acidic substance to be added is from 0.2 to 20 mols relative to 1 mol of famotidine or its salt.

9. The famotidine injection solution according to claim 1, wherein the acidic substance is one or two or more compounds selected from the group consisting of hydrochloric acid, lactic acid, L-aspartic acid, L-glutamic acid, benzoic acid, citric acid, malic acid, ascorbic acid, erythorbic acid, gluconic acid, acetic acid, and nicotinic acid.

10. The famotidine injection solution according to claim 1, wherein the water-soluble acid amide is one or two or more compounds selected from the group consisting of nicotinic acid amide, isonicotinic acid amide, and N,N-dimethylacetamide.

11. The famotidine injection solution according to claim 1, wherein the acidic substance is lactic acid, L-aspartic acid, or L-glutamic acid.

* * * * *